(12) United States Patent
Johnson

(10) Patent No.: US 9,427,349 B2
(45) Date of Patent: Aug. 30, 2016

(54) COMPACT ATHLETIC BRACE

(71) Applicant: Christopher Johnson, Cary, NC (US)

(72) Inventor: Christopher Johnson, Cary, NC (US)

( * ) Notice: Subject to any disclaimer, the term of this patent is extended or adjusted under 35 U.S.C. 154(b) by 189 days.

(21) Appl. No.: 14/210,023

(22) Filed: Mar. 13, 2014

(65) Prior Publication Data

US 2015/0257913 A1    Sep. 17, 2015

(51) Int. Cl.
*A61F 5/00* (2006.01)
*A61F 5/01* (2006.01)

(52) U.S. Cl.
CPC .............. *A61F 5/0125* (2013.01); *A61F 5/013* (2013.01)

(58) Field of Classification Search
CPC .............. A61F 5/0123; A61F 5/0125; A61F 2005/0179; A61F 2005/0139; A61F 2005/0137; A61F 5/0102; A61F 2005/0165; A61F 2005/0158; A61F 2005/0167; A61F 2005/0172; A61F 2005/0169; A61F 5/0127
USPC ................... 602/16, 23–28, 60–62; 128/882
See application file for complete search history.

(56) References Cited

U.S. PATENT DOCUMENTS

| | | | | |
|---|---|---|---|---|
| 3,817,244 | A * | 6/1974 | Taylor | A61F 5/0123 602/26 |
| 4,379,463 | A * | 4/1983 | Meier | A61F 5/0123 128/DIG. 15 |
| 5,168,577 | A * | 12/1992 | Detty | A41D 13/08 2/16 |
| 5,641,322 | A | 6/1997 | Silver | |
| 6,290,664 | B1 | 9/2001 | Nauert | |
| 7,819,830 | B2 | 10/2010 | Sindel | |
| 2007/0185423 | A1 | 8/2007 | Brown | |
| 2011/0071449 | A1 | 3/2011 | Kuhler | |
| 2011/0201983 | A1* | 8/2011 | Swanson | A61F 5/0125 602/16 |
| 2012/0010548 | A1 | 1/2012 | Scholtes | |
| 2012/0065562 | A1* | 3/2012 | Kaphingst | A61F 5/0111 602/12 |
| 2013/0289458 | A1 | 10/2013 | Okada | |
| 2014/0074002 | A1* | 3/2014 | Swanson | A61F 5/0125 602/16 |

* cited by examiner

*Primary Examiner* — Michael Brown

(57) ABSTRACT

The present invention provides an athletic brace which is composed of a flexible sleeve and a rigid framed brace. An elastic tubular shaped fabric sleeve is first placed over the elbow or knee joint and has upper front and lower rear raised lips that are used to prevent the rigid and compact framed brace from slipping downwards during usage. The tight fit of the rigid brace inside the raised lip gaps of the sleeve prevents the framed brace from slipping down from the elbow or knee joint during usage. This brace is designed to also be compact in size to allow for everyday wear in both contact and non-contact sports for both elbow and knee protection.

5 Claims, 5 Drawing Sheets

COMPACT ATHLETIC BRACE

FIELD OF THE INVENTION

The present invention relates to athletic braces, and more particularly to a compact design athletic brace that uses a combination of both rigid and elastic components to give it unique capabilities for everyday use in both contact and non-contact sports.

BACKGROUND OF THE INVENTION

Athletic braces in prior art generally fall into two general categories. The first common category is athletic braces made of a lightweight fabric and are usually tubular shaped to fit tightly over the elbow or knee joints. A second common category are athletic braces that are made from rigid elements that are hinged near the pivot point of the knee or elbow joint and are strapped directly onto the skin. Both of these prior art categories have limitations especially with athletes that want to wear athletic braces during their normal workouts to help prevent injuries to their elbow or knee joints.

Athletic braces that are made of lightweight fabric sleeves have the advantage of everyday usage by athletes because they are simple and easy to put on and the lightweight fabrics available today breathe well and do not irritate the skin. However, these fabric based athletic braces do not offer a high degree of support for the joint and many users of this type of athletic brace complain that they do not protect them enough against elbow or knee injuries especially when playing more demanding sports such as football and basketball. The main design flaw in these flexible designs is that they are too flexible and allow twisting of the elbow or knee joints when running and throwing objects.

In the case of rigid fully framed type athletic braces, essentially the opposite problems occur. Typical users of framed athletic braces complain that they are too large and bulky for everyday use and are so rigid that they cannot flex the elbow or knee joints enough to gain competitive advantages such as a wide receiver attempting to maneuver around a defensive player while leaping for a pass in football.

Indeed, there is a need to provide a better athletic brace that the modern athlete can wear everyday as they practice on the field and can address these noted deficiencies in the prior art.

BRIEF SUMMARY OF THE INVENTION

It is an object of the present invention to provide an athletic brace that is both lightweight and compact in size with a total length of preferably around eight inches and a total weight of approximately one pound.

It is yet another object of the present invention to provide an athletic brace that includes a slip resistant neoprene sleeve with a set of raised lips to keep the framed brace properly placed and aligned around the joint to be protected.

It is yet another object of the present invention to provide an athletic brace that can be used for both knee and elbow joint protection applications.

DETAILED DESCRIPTION OF THE INVENTION

Figure 1:
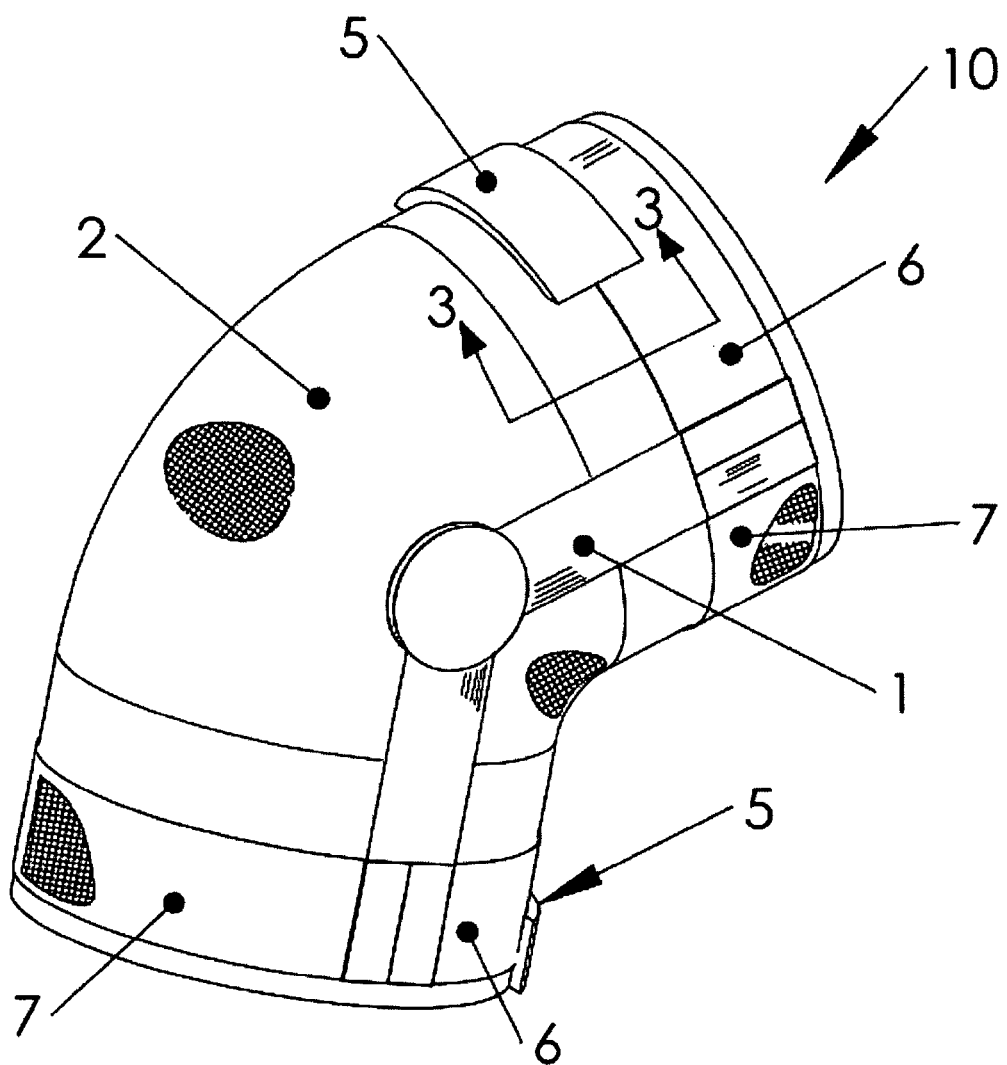
FIG. 1 is a perspective view of the compact athletic brace of the present invention.

Referring now to the drawings and in particular FIG. 1, an athletic brace according to the present invention is generally designated by reference numeral 10. Athletic brace 10 consists of a compact framed brace 1 and a flexible sleeve 2. The flexible sleeve 2 in the preferred embodiment is made of a lightweight fabric that is strong and flexible, preferably a material such as neoprene rubber. The brace wearer would first slide the sleeve 2 over their hand or foot and pull the sleeve up to fit snugly over the knee or elbow joint. In the preferred embodiment, the sleeve 2 would be a continuous molded sleeve and not stitched together. Various sized sleeves would be molded to fit a large range of knee and elbow joint sizes for both men and women.

Figure 2:
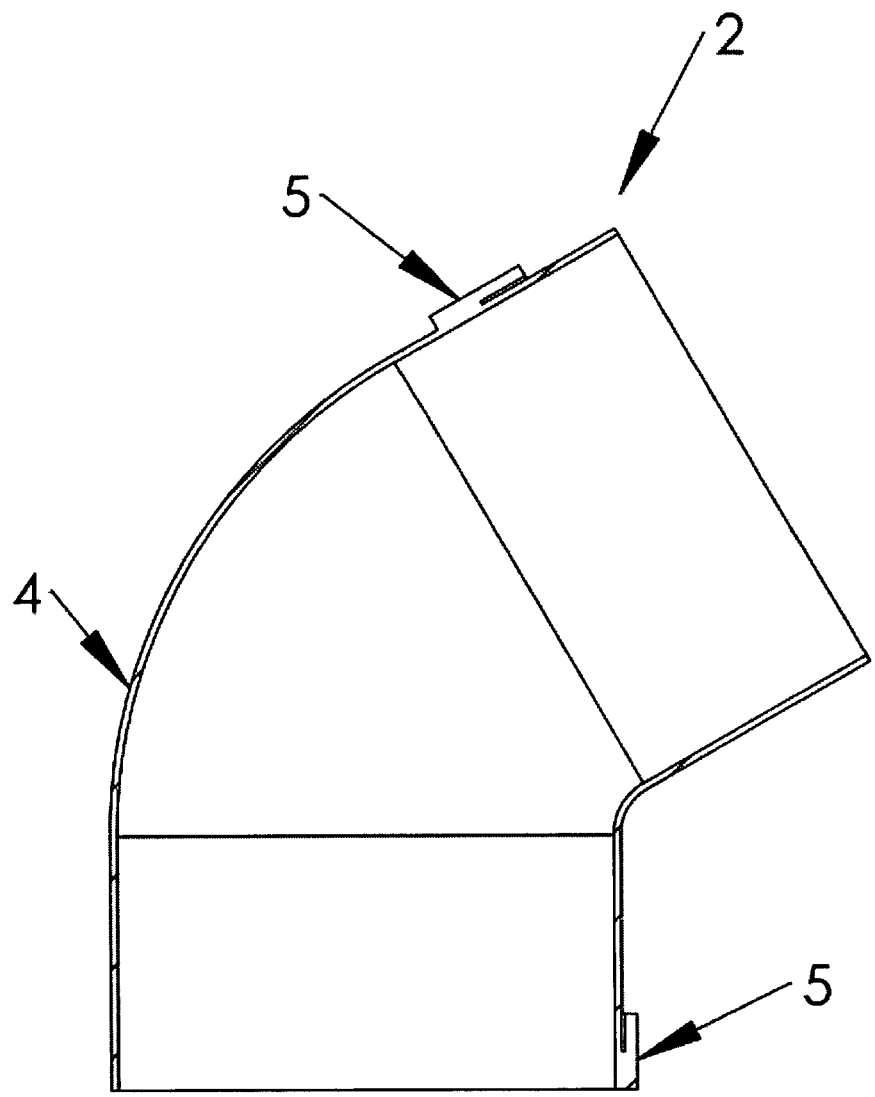
FIG. 2 is a cross sectional view of the flexible sleeve component of the athletic brace.

Referring next to FIGS. 1 & 2, sleeve 2 is shown to have raised lips 5 located at the front side of the sleeve for the upper raised lip and at the back side of the sleeve for the lower raised lip. In the preferred embodiment as shown in FIG. 1, the upper raised lip 5 covers only a fraction of the front half of the sleeve and the lower raised lip covers only a fraction of the rear half of the sleeve. In the preferred embodiment the raised lips 5 are molded into the main body 4 of the sleeve 2. The sleeve 2 is preferably made of an elastic material such as neoprene rubber material. Neoprene rubber also has a high degree of friction which will provide the athletic brace 10 an added degree of improved slip resistance during usage as compared with typical framed braces of the prior art.

Figure 3:
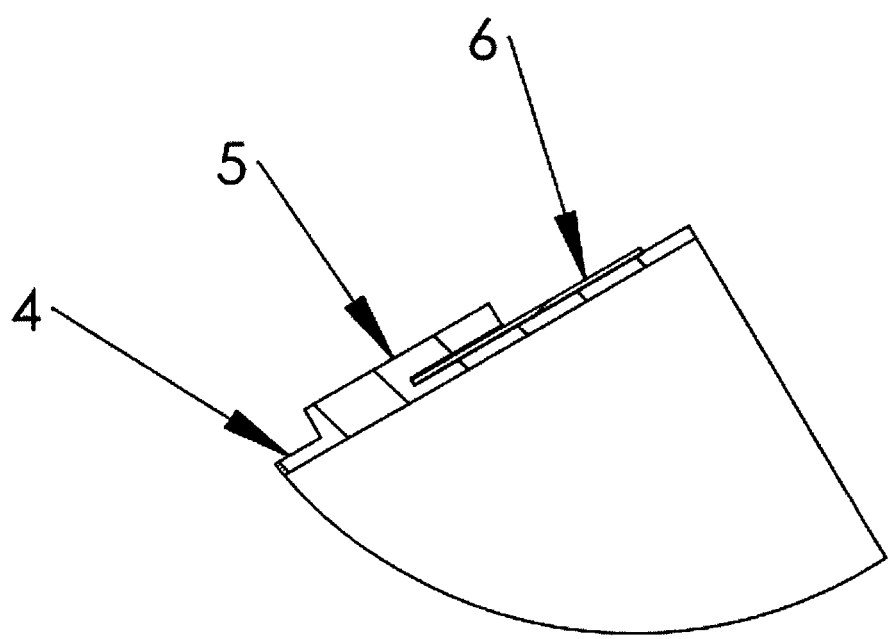
FIG. 3 is a detailed view of the upper raised lip portion of the flexible sleeve.

FIG. 3 shows a cross sectional view of the upper raised lip 5 and rigid arched support 6 (through line 3-3 previously drawn in FIG. 1) in order to show a close up view of how the rigid arched support 6 fits inside the raised lip 5 of sleeve 2. The raised lip creates a slight gap which allows the rigid arched support 6 to fit inside thus forming a tight fit between the two components.

Figure 4:
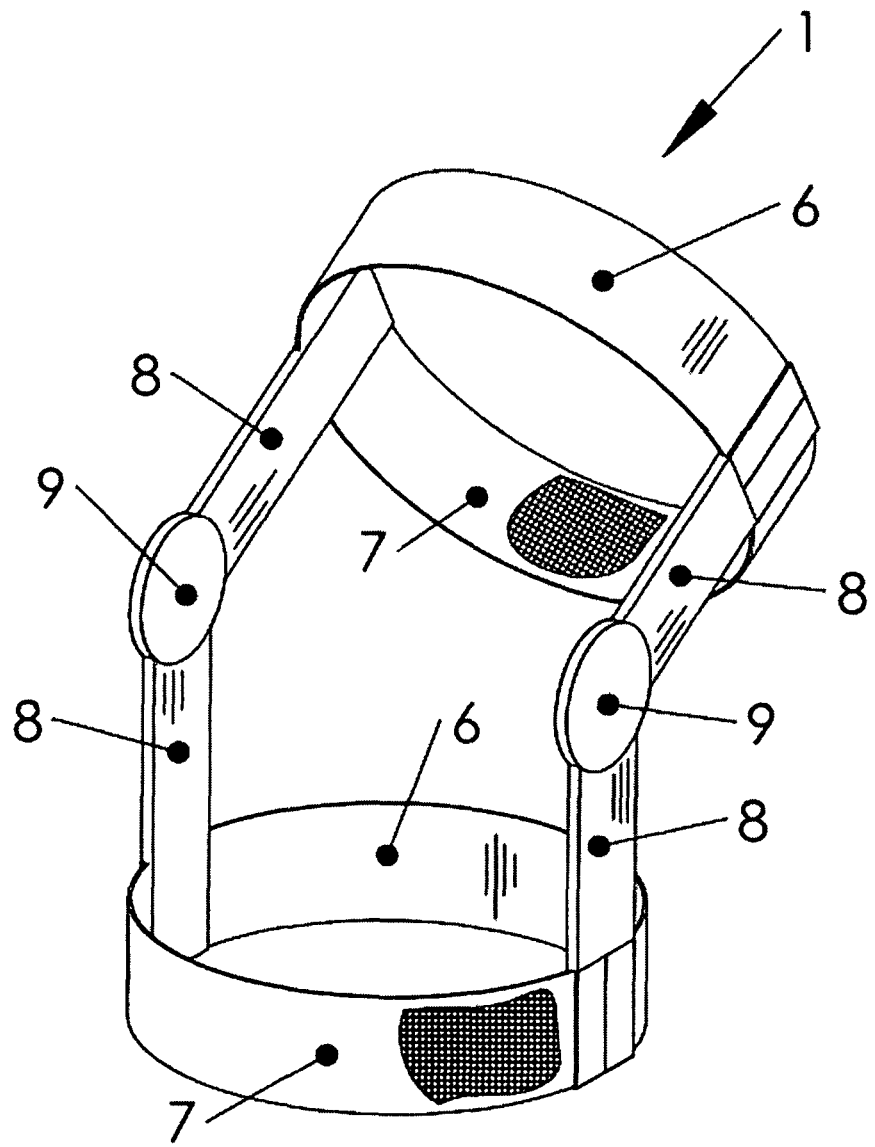
FIG. 4 is a perspective view of the rigid framed brace component of the athletic knee or elbow brace.

Referring next to FIG. 4, the rigid framed brace 1 is shown in perspective view to show the various components of its construction. Framed brace 1 consists of a combination of rigid and flexible support components. The rigid components are preferably made from lightweight and strong materials such as aluminum or carbon fiber composite. The flexible materials in the preferred embodiment may be made from lightweight and flexible materials including neoprene rubber or Velcro strap. The components that together form a rigid brace frame are the vertical support bars 8 and the upper front and lower rear rigid arched supports 6. In order to form a compact athletic brace, the length of the vertical support bars 8 is preferably between 3 and 4 inches for use in knee braces and is preferably between 2 to 3 inches for use in elbow braces. The center hinge 9 allows for limited angular movement of the athletic brace frame 10 during use and each hinge 9 is rigidly attached to both upper and lower vertical support bars 8 on each side of said framed brace 1.

Referring again to FIG. 4, the flexible components of rigid framed brace 1 consist of both upper rear and lower front flexible support straps 7. The flexible straps 7 may be secured to the upper front and lower rear rigid arched supports 6 by several well known methods in the art of making athletic braces including Velcro, clips or button snaps.

It will be obvious to those skilled in the art of making athletic braces that modifications may be made to the embodiments described above without substantially departing from the scope of the present invention. For example, an alternative embodiment of the present invention is for the wearer to only use the rigid framed brace 1 without said sleeve 2.

Figure 5:
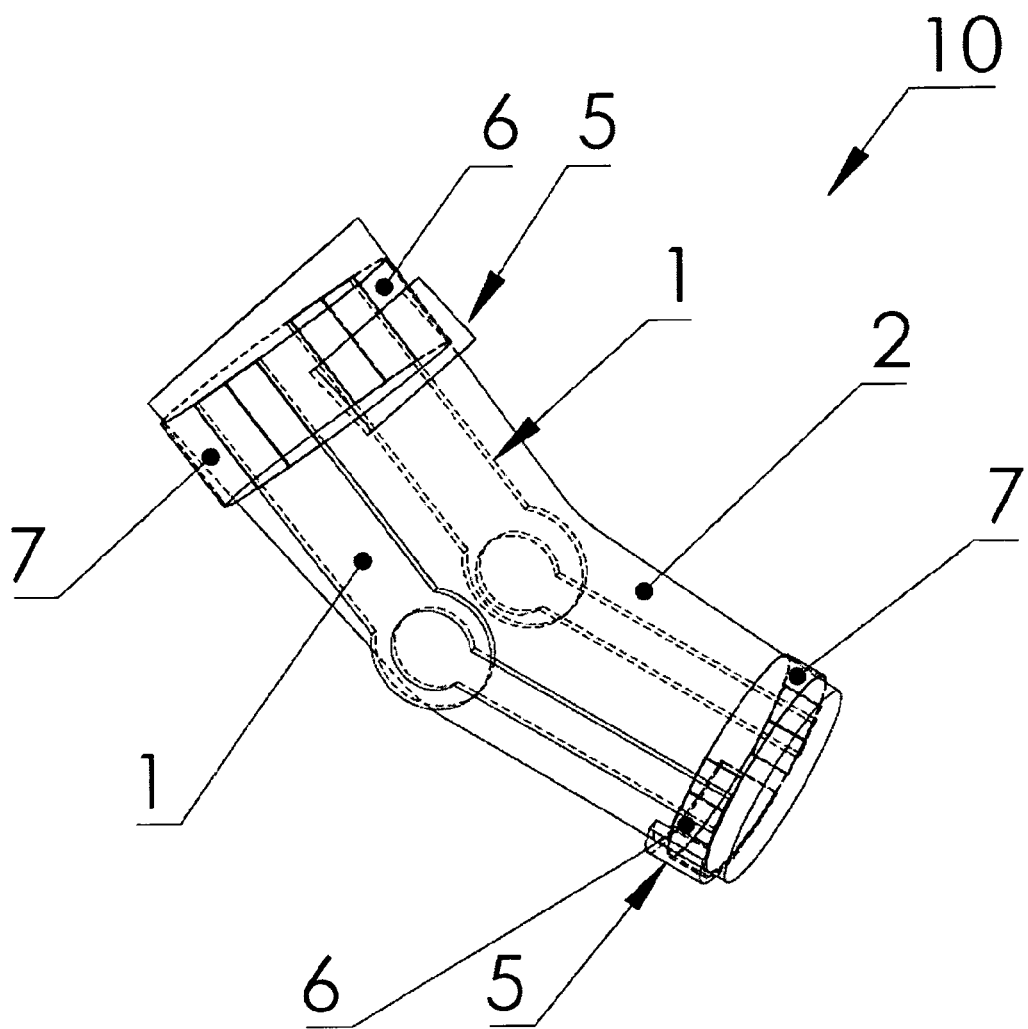
FIG. 5 is a perspective view of the compact athletic elbow brace of the present invention.

Referring finally to FIG. 5, the compact athletic brace 10 is shown in an elbow embodiment. Brace 10 again consists of a fabric sleeve 2 that further contains raised lips 5 at the top frontal portion of the upper arm and at the back rear portion of the lower arm below the elbow joint as shown in the drawing. Said rigid brace frame 1 then is fit on such that the rigid arches 6 fit inside the lip pocket of raised lips 5 thus providing a secure fit. Finally, said securing straps 7 wrap around the sleeve 2 to provide additional security to prevent the brace frame from sliding off said sleeve 2 during movement.

What is claimed is:

1. An athletic brace comprising a sleeve made of a moldable rubber compound, said sleeve having an upper raised lip portion extending directly from the front outer surface of said sleeve and a lower raised lip extending directly from the rear outer surface of said sleeve, said upper and lower lips having an open portion therein, a rigid frame member having an upper front and a lower rear rigid arch support part connected together by a pair of upper support bars and a pair of lower support bar, that are pivotally connect via a centrally located hinge component, the upper front arch frame member is located inside of the open portion of the upper raised lip portion and the lower rear arch frame member is located inside of the open portion of the lower raised lip portion, said sleeve is elongated and extends along the entire length of the frame member.

2. The athletic brace of claim 1, wherein the total combined length of the rigid brace support bars is between five to six inches in length.

3. The athletic brace of claim 1, wherein the total combined weight of the sleeve and the frame member is approximately one pound.

4. The athletic brace of claim 1, wherein a pair of upper rear and lower front flexible straps are adapted to secure the knee to the upper front and lower rigid arch members.

5. The athletic brace of claim 1, wherein the rigid frame brace is adapted to be applied to the knee without the use of the sleeve.

* * * * *